US006121288A

United States Patent [19]

Masui et al.

[11] Patent Number: 6,121,288

[45] Date of Patent: Sep. 19, 2000

[54] VISCERAL FAT LOWERING AGENT

[75] Inventors: Seiichiro Masui, Ageo; Yoshihisa Nakano, Yokohama, both of Japan

[73] Assignee: Nippon Chemiphar Co., Ltd., Tokyo, Japan

[21] Appl. No.: 09/297,800

[22] PCT Filed: Nov. 7, 1997

[86] PCT No.: PCT/JP97/04051

§ 371 Date: May 6, 1999

§ 102(e) Date: May 6, 1999

[87] PCT Pub. No.: WO98/20871

PCT Pub. Date: May 22, 1998

[30] Foreign Application Priority Data

Nov. 8, 1996 [JP] Japan .................................... 8-312770

[51] Int. Cl.[7] ................... A61K 31/4709; A61K 31/427; A61K 31/426; A61P 3/04

[52] U.S. Cl. .......................... 514/314; 514/337; 514/339; 514/342; 514/369

[58] Field of Search .................................... 514/314, 337, 514/339, 342, 369

[56] References Cited

U.S. PATENT DOCUMENTS 4,572,912 2/1986 Yoshioka ................................ 514/369
4,687,777 8/1987 Meguro .................................. 514/342

FOREIGN PATENT DOCUMENTS

96/12719 5/1996 WIPO .

OTHER PUBLICATIONS

Yamashita S et al. Diabetes Care. 19 (3) 287–91, Mar. 1996.

*Primary Examiner*—Evelyn Mei Huang
*Attorney, Agent, or Firm*—Reed Smith Shaw & McClay LLP

[57] ABSTRACT

Methods for decreasing visceral fat, inhibiting accumulation of visceral fat and improving the distribution of visceral fat all include the administration of a thiazolidine derivative represented by formula (IV), (IV)

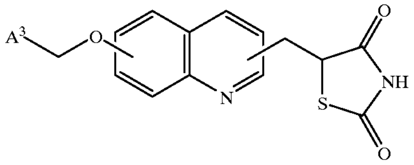

wherein $A^3$ represents an optionally substituted phenyl or oxazolyl group.

9 Claims, No Drawings

VISCERAL FAT LOWERING AGENT

This application is the national phase of PCT/JP97/04051, filed on Nov. 7, 1997.

[FIELD OF THE INVENTION]

This invention relates to medicinal compositions for inhibiting visceral fat accumulation (which is now understood to cause diseases such as hypertension, diabetes, hyperlipemia, and arteriosclerosis), for decreasing visceral fat, and for improving body fat distribution. In particular, the invention relates to a visceral fat decreasing agent, a visceral fat accumulation inhibitor, and a body fat distribution improver each of which comprises a thiazolidine or oxazolidine derivative as the active ingredient.

[BACKGROUND OF THE INVENTION]

Recently, the relationship between diseases and the body fat distribution has been studied. According to the study, even in a non-obese person as well as an obese person, visceral fat accumulation in the abdominal cavity (particularly, in the mesentery and/or in the greater omentum) positively correlates with values of serum cholesterol, triglyceride, and blood glucose measured by the glucose tolerance test. Further, the visceral fat accumulation also positively correlates with the systolic and diastolic blood pressures, and accordingly it highly relates to diseases such as hypertension, diabetes, and hyperlipemia [Fujioka, S., et al. Metabolism, 36 54–59, 1987; Matsuzawa, Y., et al. Progress in Obesity Research, 309–312, 1990]. These diseases are, therefore, thought to be cured or prevented by decreasing visceral fat, by inhibiting visceral fat accumulation, or improving body fat distribution [Bray, G. A., Obesity Research, 3, Suppl. 4, 425S–434S, 1995].

For decreasing body fat, treatments such as ergo-therapy, diet, behavior therapy, and pharmacotherapy are practically employed. In the pharmacotherapy, an anorectic agent working on the central nervous system is employed, and a $\beta_3$-adrenergic receptor stimulant and a fat absorption inhibitor have been developed. However, these so-called "anti-obesity drugs" are not thought to be effective for decreasing visceral fat, and hence there is no effective pharmacotherapy for decreasing visceral fat.

The relationship between insulin sensitivity and body fat distribution has been also studied, and it suggests that insulin sensitivity is caused by the visceral fat accumulation. Accordingly, it is commonly understood that visceral fat accumulation causes the above-mentioned diseases accompanied by insulin sensitivity or independently thereof.

Thiazolidine derivatives which improve insulin sensitivity are already known to effectively serve as blood glucose depressors or blood lipid depressors [Japanese Patent Provisional Publications No. 61(1986)-267580 and No. 60(1985)-51189, and WO 96/12719]. On the other hand, however, some of these derivatives are reported to promote appetite and increase the body weight. Further, it is also reported that they increase brown adipocyte in rodents and promote the differentiation of preadipocyte into adipocyte in vitro. In view of those reports, the thiazolidine derivatives are generally believed to rather increase the body fat.

Accordingly, although the relationship between insulin sensitivity and visceral fat accumulation is noticed, no insulin sensitizer serving for decreasing visceral fat has been developed.

[DISCLOSURE OF THE INVENTION]

The inventors studied on thiazolidine or oxazolidine derivatives improving insulin sensitivity, and surprisingly found that some of these derivatives also decrease visceral fat, inhibit visceral fat accumlation, and improve body fat distribution.

It is an object of the present invention to provide a visceral fat decreasing agent, a visceral fat accumulation inhibitor and a body fat distribution improver each of which comprises a thiazolidine or oxazolidine derivative as an active ingredient.

The present invention resides in a visceral fat decreasing agent which comprises as an active ingredient a compound of the following formula (I):

$$A^1—X^1—B^1—Y^1—C^1—D—E \quad (I)$$

wherein $A^1$ represents an optionally substituted cyclo-alkyl, aryl, or heterocyclic group; $X^1$ represents a bond, an oxygen atom, a sulfur atom, or $N(R^1)$ in which $R^1$ is a hydrogen atom, an alkyl or aralkyl group; $B^1$ represents an optionally substituted alkylene chain; $Y^1$ represents a bond, an oxygen atom, a sulfur atom, or $N(R^2)$ in which $R^2$ is a hydrogen atom, an alkyl group or an aralkyl group; $C^1$ represents an optionally substituted divalent aryl, mono-cyclic unsaturated hydrocarbon, or heterocyclic group; D represents an optionally substituted alkylene chain; and E represents a carboxylic acid, its equivalent group, or a heterocyclic group having the following formula (II):

(II)

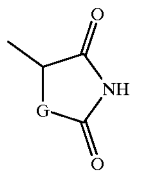

in which G represents an oxygen atom or a sulfur atom.

The invention also resides in a visceral fat accumulation inhibitor comprising a compound of the formula (I) as an active ingredient.

Further, the invention resides in a body fat distribution improver comprising a compound of the formula (I) as an active ingredient.

[PREFERRED EMBODIMENTS OF THE INVENTION]

The compound of the aforementioned formula (I) which serves as an active ingredient of a visceral fat decreasing agent, a visceral fat accumulation inhibitor and a body fat distribution improver preferably is a thiazolidine derivative having the following formula (III):

(III)

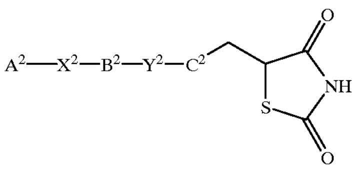

wherein $A^2$ represents an optionally substituted phenyl, pyridyl, oxazolyl, or chromanyl group; $X^2$ represents a bond or $N(R^3)$ in which $R^3$ is a hydrogen atom, or an alkyl or aralkyl group; $B^2$ represents an optionally substituted alkylene chain; $Y^2$ represents a bond or an oxygen atom; and $C^2$ represents an optionally substituted ring of benzene, quinoline, indole, or benzothiophene.

The thiazolidine derivative of the aforementioned formula (I) or the formula (III) which serves as an active ingredient of a visceral fat decreasing agent, a visceral fat accumulation inhibitor and a body fat distribution improver preferably is 5-[4-[(6-hydroxy-2,5,7, 8-tetramethylchroman-2-yl) methoxy]benzyl]-2,4-thiazoli-dinedione, 5-[4-[2-(5-ethyl-2-pyridyl)ethoxy]benzyl-2,4-thiazolidinedione, 5-[4-[2-(methyl-2-pyridylamino)-ethoxy]benzyl]-2,4-thiazolidinedione, or a thiazolidine derivative of the following formula (IV):

(IV)

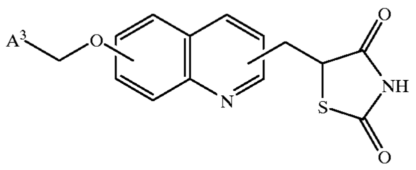

in which $A^3$ represents an optionally substituted phenyl or oxazolyl group.

Further, the thiazolidine derivative of the above-mentioned formula (IV) which serves as an active ingredient of a visceral fat decreasing agent, a visceral fat accumulation inhibitor and a body fat distribution improver preferably is 5-[(7-benzyloxy-3-quinolyl)methyl]-2,4-thiazolidinedione.

Concrete examples of each group of the compound of the formula (I) are given below in more detail.

The group represented by $A^1$ is, for example, an optionally substituted 5- to 7- membered cycloalkyl (e.g., cyclohexyl) group; an optionally substituted aryl (e.g., phenyl, naphthyl) group; or an optionally substituted 5- to 8-membered heterocyclic (e.g., pyridyl, oxazolyl, furyl, thienyl, and imidazolyl) group consisting of ring-forming carbon atoms, one or two nitrogen atom(s), and an oxygen or sulfur atom. The heterocyclic group may be a ring condensed with a benzene ring (e.g., groups of benzoxazolyl, benzoimidazolyl, benzothiazolyl, chromanyl, and imidazolyl). Examples of the substituent groups include an alkyl (e.g., methyl, ethyl, propyl, isopropyl) group having 1–6 carbon atoms, an alkoxy (e.g., methoxy, ethoxy, propoxy, isopropoxy) group having 1–6 carbon atoms, a halogen (e.g., fluorine, chlorine) atom, a 1–3 halogen-substituted alkyl (e.g., chloromethyl, trifluoromethyl) group having 1–6 carbon atoms, a 1–3 halogen-substituted alkoxy (e.g., chloromethoxy, trifluoromethoxy) group having 1–6 carbon atoms, hydroxyl group, nitro group, amino group, phenyl group, thienyl group, furyl group, thiazolyl group, and pyridyl group.

$X^1$ represents a bond, an oxygen atom, a sulfur atom, or $N(R^1)$ in which $R^1$ is a hydrogen atom, an alkyl (e.g., methyl, ethyl, propyl, isopropyl) group of 1–6 carbon atoms, or an aralkyl (e.g., benzyl, phenethyl) group comprising an alkyl group of 1–4 carbon atoms.

Examples of the groups represented by $B^1$ include an alkylene chain of 1–4 carbon atoms. The chain may be substituted with an alkyl (e.g., methyl, ethyl, propyl, isopropyl) group of 1–6 carbon atoms, an aralkyl (e.g., benzyl, phenethyl) group comprising an alkyl group of 1–4 carbon atoms, hydroxyl group, or oxo group.

$Y^1$ represents a bond, an oxygen atom, a sulfur atom, or $N(R^2)$ in which $R^2$ is a hydrogen atom, an alkyl (e.g., methyl, ethyl, propyl, isopropyl) group of 1–6 carbon atoms, or an aralkyl (e.g., benzyl, phenethyl) group comprising an alkyl group of 1–4 carbon atoms.

The group represented by $C^1$ may be an optionally substituted aryl (e.g., phenyl), monocyclic unsaturated hydrocarbon (e.g., 1,3-cyclohexadiene), or heterocyclic (e.g., benzofuran, chromanyl, quinoline, indole, benzothiophene) group. As the substituent groups, those described above for $A^1$ are also employable for $C^1$.

Examples of the groups represented by D include an alkylene chain of 1–4 carbon atoms. The chain may be substituted with an alkyl (e.g., methyl, ethyl, propyl, isopropyl) group of 1–6 carbon atoms, or an aralkyl (e.g., benzyl, phenethyl) group comprising an alkyl group of 1–4 carbon atoms. The alkylene chain may partly comprise an unsaturated bond.

The group represented by E is, for example, a carboxylic acid, its equivalent group (e.g., nitrile, ester), or a heterocyclic group having the following formula (II):

(II)

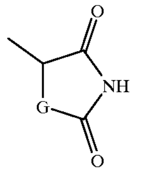

in which G is as defined previously.

Concrete examples of each group of the thiazolidine derivative of the formula (III) are given below.

The group of $A^2$ is an optionally substituted phenyl, pyridyl, oxazolyl, or chromanyl group. Examples of the substituent groups are the same as those described above for $A^1$. Preferred substituent groups are an alkyl (e.g., methyl, ethyl, propyl, isopropyl) group having 1–6 carbon atoms, an alkoxy (e.g., methoxy, ethoxy, propoxy, isopropoxy) group having 1–6 carbon atoms, a 1–3 halogen-substituted alkyl (e.g., trifluoromethyl) group having 1–6 carbon atoms, a 1–3 halogen-substituted alkoxy (e.g., trifluoromethoxy) group having 1–6 carbon atoms, hydroxyl group, and phenyl group.

$X^2$ represents a bond or $N(R^3)$ in which $R^3$ is a hydrogen atom, an alkyl (e.g., methyl, ethyl, propyl, isopropyl) group having 1–6 carbon atoms, or an aralkyl (e.g., benzyl, phenethyl) group comprising an alkyl group of 1–4 carbon atoms. Preferably, $X^2$ is a bond.

The group of $B^2$ can be the same as that of $B^1$ in the formula (I), and is preferably methylene or ethylene.

$Y^2$ represents a bond or an oxygen atom, and $C^2$ represents an optionally substituted benzene ring, quinoline ring, indole ring, or benzothiophene ring. As the substituent groups, those described above for $A^2$ are also employable for $C^2$.

Concrete examples of the groups of $A^3$ in the thiazolidine derivative of the formula (IV) are given below in more detail.

The group of $A^3$ is an optionally substituted phenyl or oxazolyl group. Examples of the substituent group are the same as those described above for $A^1$. Preferred substituent groups are an alkyl (e.g., methyl, ethyl, propyl, isopropyl) group having 1–6 carbon atoms, an alkoxy (e.g., methoxy, ethoxy, propoxy, isopropoxy) group having 1–6 carbon atoms, a 1–3 halogen-substituted alkyl (e.g., trifluoromethyl) group having 1–6 carbon atoms, a 1–3 halogen-substituted alkoxy (e.g., trifluoromethoxy) group having 1–6 carbon atoms, hydroxyl group and phenyl group. The groups of $A^3CH_2O$— and 2,4-thiazolidinedion-5-yl methyl are preferably positioned at the 6- or 7-position and at the 3-position of the quinoline ring, respectively.

The compound of the formula (I) and the thiazolidine derivative of the formula (III) can be prepared by the method described in Japanese Patent Provisional Publications No. 61-267580 and No. 60-51189, and WO 96/12719.

In general, that compound or derivative may have an asymmetric carbon atom (for example, the carbon atom at the 5-position of thiazolidine ring in the formula (III) is asymmetric), and hence the above-mentioned formulas include optical isomers and racemic bodies. Further, geometric isomers (i.e., cis-isomer and trans-isomer) are also included in the formulas.

The above-mentioned compound or derivative can be used in the form of a pharmaceutically acceptable salt. Examples of the salts include a basic salt such as an alkaline metal (e.g., sodium, potassium) salt and an organic amine (e.g., methylamine) salt, and an acidic salt such as a salt of mineral acid (e.g., hydrochloride, hydrobromide) and a salt of an organic acid (e.g., acetate, fumarate).

Typical examples of the thiazolidine derivatives of the formula (III) are set forth in Table 1. Those derivatives are preferably incorporated in the medicinal composition of the invention as the active ingredient.

TABLE 1

| | $A^2$ | $X^2$ | $B^2$ | $Y^2$ | $C^2$ |
|---|---|---|---|---|---|
| 1 | 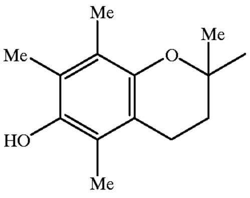 | Bond | $—CH_2—$ | O | 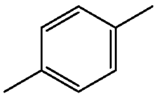 |
| 2 | 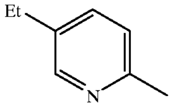 | Bond | $—(CH_2)_2—$ | O | 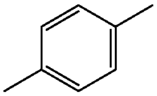 |
| 3 | 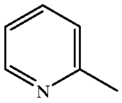 | —NMe | $—(CH_2)_2—$ | O | 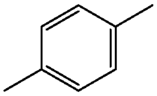 |
| 4 | 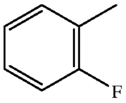 | Bond | $—CH_2—$ | O | 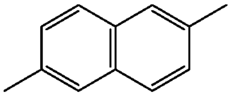 |
| 5 | 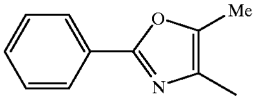 | Bond | $—(CH_2)_2—$ | O | 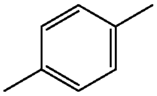 |
| 6 | 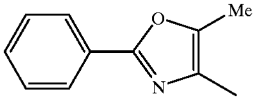 | Bond | $—(CH_2)_2CO—$ | Bond | 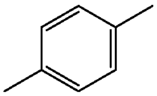 |
| 7 | 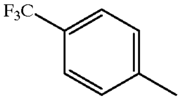 | Bond | $—CH_2—$ | O | 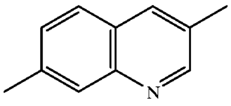 |
| 8 | 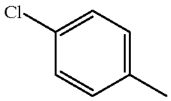 | Bond | $—CH_2—$ | O | 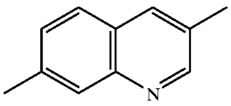 |
| 9 | 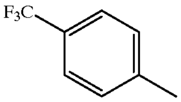 | Bond | $—CH_2—$ | O | 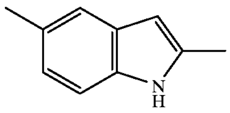 |

TABLE 1-continued

| | $A^2$ | $X^2$ | $B^2$ | $Y^2$ | $C^2$ |
|---|---|---|---|---|---|
| 10 | 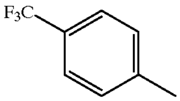 | Bond | $—CH_2—$ | O | 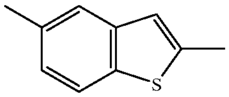 |

Typical examples of compounds of the formula (I) other than the thiazolidine derivative of the formula (III) are set forth in Table 2. Those compounds are also preferably incorporated into the medicinal composition of the invention as an active ingredient.

TABLE 2

| | $A^1$ | $X^1$ | $B^1$ | $Y^1$ | $C^1$ | D | E |
|---|---|---|---|---|---|---|---|
| 1 | 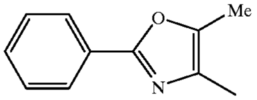 | Bond | $—(CH_2)_2—$ | O | 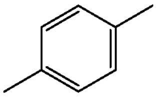 | $—(CH_2)_3—$ | 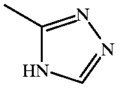 |
| 2 | 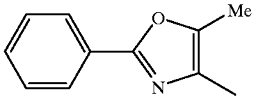 | Bond | $—(CH_2)_2—$ | O | 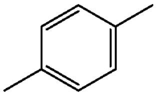 | 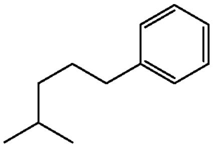 | $—CO_2H$ |
| 3 | 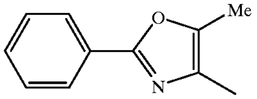 | Bond | $—(CH_2)_2—$ | O | 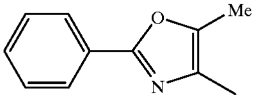 | $—CH_2—$ | 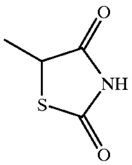 |
| 4 | 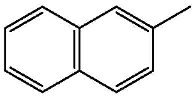 | Bond | $—CH_2—$ | Bond | 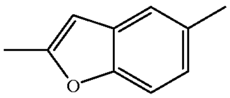 | $—CH_2—$ | 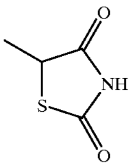 |
| 5 | 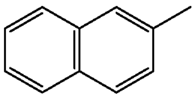 | Bond | $—(CH_2)_3—$ | Bond | 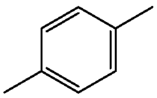 | $—CH_2—$ | 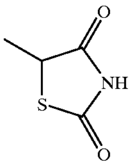 |
| 6 | 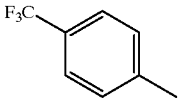 | Bond | $—CH_2—$ | O | 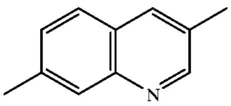 | $—CH_2—$ | 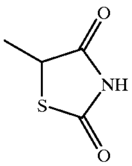 |
| 7 | 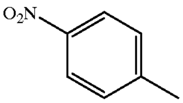 | Bond | $—CH_2—$ | O | 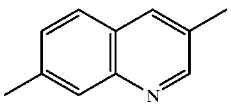 | $—CH_2—$ | 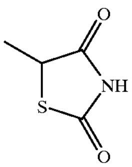 |

TABLE 2-continued

| | $A^1$ | $X^1$ | $B^1$ | $Y^1$ | $C^1$ | D | E |
|---|---|---|---|---|---|---|---|
| 8 | 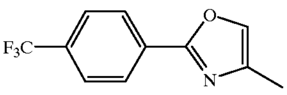 | Bond | $—CH_2—$ | O | 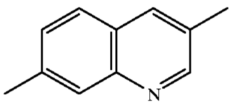 | $—CH_2—$ | 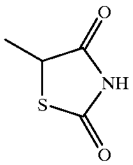 |
| 9 | 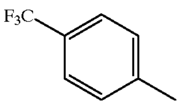 | Bond | $—CH_2—$ | O | 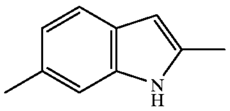 | $—CH_2—$ | 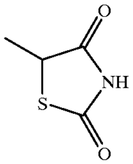 |
| 10 | 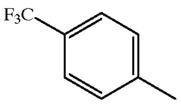 | Bond | $—CH_2—$ | O | 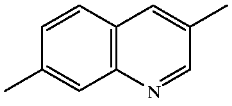 | 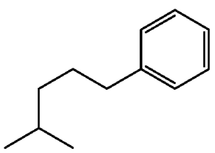 | $—CO_2H$ |

Results of the pharmacological tests of the invention are described below.

The below-described Examples 1 to 4 have revealed that the compound of the formula (I) or thiazolidine derivative of the formula (I) decreases visceral fat, inhibits visceral fat accumulation, and improves body fat distribution.

In Example 1, an active ingredient of the invention (5-[[7-(4-trifluoromethyl)benzyloxy-3-quinolyl]methyl]-2,4-thiazolidinedione: Compound 1) was given to rats at a dosage of 100 mg/kg, and it was confirmed that the size of mesenteric adipose tissue of the dosed rats (experimental group) decreased to 72% as compared with that of the control group.

Further, it was also found in Example 2 that the above-mentioned compound reduced the weight of the mesenteric adipose tissue in a dose-dependent manner.

In Example 3, another active ingredient of the invention (5-[(7-benzyloxy-3-quinolyl)methyl]-2,4-thiazolidinedione: Compound 7) was given to KKAy male mice (experimental group), and it was confirmed that this compound significantly improved body fat distribution as compared with the control group.

Further, it was also found in Example 4 that the above-mentioned compound significantly decreased the size of mesenteric tissue as compared with the control group.

These results indicate that the compound of the formula (I) or thiazolidine derivative of the formula (III) is advantageously employable as a visceral fat decreasing agent, a visceral fat accumulation inhibitor, or a body fat distribution improver.

The inventors has already reported the thiazolidine derivatives in which the group of $C^2$ in the formula (III) is quinoline [WO 96/12719], and the group of $C^2$ is indole or benzothiophenone [Japanese Patent Application No. 8-99084]. Those compounds decrease blood glucose and lipid.

The medicinal compositions (i.e., visceral fat decreasing agent, visceral fat accumulation inhibitor, and body fat distribution improver) of the invention, each of which comprises as an active ingredient a compound of the formula (I) or a thiazolidine derivative of the formula (III), can be administered orally (for example, in the form of tablets, capsules or granules) or parenterally (for example, in the form of injection or suppository). For preparing the pharmaceutical compositions, conventional additives are generally incorporated. Examples of the additives include excipients (e.g., glucose, lactose), disintegrators (e.g., starch, carboxymethyl cellulose calcium (CMC-Ca)), binders (e.g., hydroxypropyl cellulose (HPC), polyvinylpyrrolidone (PVP)), lubricants (e.g., talc, magnesium stearate), diluents, and dyes.

For an adult, the dose of the compound of the formula (I) or a thiazolidine derivative of the formula (III) is usually in the range of 0.1 mg/day to 100 mg/day (in the case of injection) or 1 mg/day to 10.0 g/day (in the case of oral administration). Generally, the dose is determined according to various conditions such as the age and the symptoms of the patient.

The pharmacotherapy using the pharmaceutical composition comprising a compound of the formula (I) or a thiazolidine derivative of the formula (III) may be performed singly or in combination with other treatments such as ergotherapy and dietetic treatment.

[EXAMPLES]

In the following examples, the present invention is further described in more detail.

Example 1: Decrease of Cell Size of Mesenteric Adipose Tissue

Procedure

A group consisting of four or five SD female rats aged 5 weeks was prepared. To the group, a sample suspended in 1% aqueous solution of methyl cellulose was orally administered once a day for 4 weeks. Each of thus treated rats was dissected to collect the mesenteric adipose tissue, and then the tissue was sliced to prepare a paraffin specimen for microscope. After hematoxylin-eosin staining, micrographs of each specimen were randomly taken. From the micrographs, the area occupied by one adipocyte was estimated on average. In Table 3, the average adipocyte area of each experimental group was shown in a relative value which is calculated under the condition that an average adipocyte area of the control group was set at 100%.

Results

The results are set forth in Table 3.

TABLE 3

| Decrease of Cell Size of Mesenteric Adipose Tissue | | | |
|---|---|---|---|
| sample* | dose | number of rats | adipocyte area (%) |
| Control | 0 | 5 | 100 |
| Compound 1 | 100 | 5 | 72 |
| Compound 2 | 30 | 5 | 57 |
| Compound 3 | 30 | 4 | 64 |
| Compound 4 | 100 | 4 | 43 |
| Compound 5 | 100 | 5 | 72 |
| Compound 6 | 400 | 5 | 69 |

*) The samples are as follows: Compound 1: 5-[[7-(4-trifluoromethyl) benzyloxy-3-quinolyl]methyl]-2,4-thiazolidinedione, Compound 2: 5-[[5-(4-trifluoromethyl)benzyloxy-2-indolyl]methyl]-2,4-thiazolidinedione, Compound 3: 5-[[6-(4-trifluoromethyl)benzyloxy-2-indolyl[methyl]-2,4-thiazolidinedione, Compound 4: 5-[[6-(4-trifluoromethyl)benzyloxy-2-benz [b]thienyl]methyl]-2,4-thiazolidinedione,Compound 5: 5-[4-[2-(5-ethyl-2-pyridyl)ethoxy]benzyl]-2,4-thiazolidinedione, and Compound 6: 5-[4-[(6-hydroxy-2,5,7,8-tetramethyl-chroman-2-yl)methoxy]benzyl]-2,4-thiazolidinedione.

The results shown in Table 3 indicate that Compounds 1–6, which are the compounds of the formula (I) or the thiazolidine derivatives of the formula (III), decrease of cell size of mesenteric adipose tissue.

Example 2: Weight Reduction of Mesenteric Adipose Tissue

Procedure

A group consisting of five SD female rats aged 5 weeks was prepared. To the group, the sample suspended in 1% aqueous solution of methyl cellulose was orally administered once a day for 13 weeks. Each of thus treated rats was dissected to collect the mesenteric adipose tissue, and then the wet tissue weights were measured. The measured weight was normalized to a value per 100 g of body weight, and the average was calculated.

Results

The results are set forth in Table 4.

TABLE 4

| Weight Reduction of Mesenteric Adipose Tissue | | | |
|---|---|---|---|
| sample* | dose (mg/kg) | number of rats | weight af adipose tissue per 100 g of body weight |
| Control | 0 | 7 | 1.26 |
| Compound 1 | 10 | 7 | 1.00 |
| Compound 1 | 30 | 7 | 0.92 |
| Compound 1 | 100 | 7 | 0.78 |
| Compound 5 | 100 | 7 | 1.05 |

*) The samples are as follows: Compound 1: 5-[[7-(4-trifluoromethyl) benzyloxy-3-quinolyl]methyl]-2,4-thiazolidinedione, and Compound 5: 5-[4-[2-(5-ethyl-2-pyridyl)ethoxy]benzyl]-2,4-thiazolidinedione.

The results shown in Table 4 indicate that Compounds 1 and 5, which are the compounds of the formula (I) or thiazolidine derivatives of the formula (III), reduce the weight of the mesenteric adipose tissue.

Example 3: Improvement of Body Fat Distribution

A group consisting of four or five KKAy male mice aged 16 weeks was prepared. To the group, the sample was administered as a food admixture for 15 days. Each of thus treated rats was dissected to collect the mesenteric and dorsal subcutaneous adipose tissue, and then the wet tissue weights were measured. The weight ratio of the mesenteric tissue to the subcutaneous tissue (m/s ratio) was calculated to estimate the body fat distribution. In Table 5, the average m/s ratio of the group was shown.

TABLE 5

| Improvement of Body Fat Distribution | | | |
|---|---|---|---|
| sample* | dose | number of rats | m/s ratio |
| Control | 0 | 5 | 0.574 |
| Compound 6 | 0.3% | 4 | 0.541 |
| Compound 7 | 0.1% | 5 | 0.454 |

*) The samples are as follows: Compound 6: 5-[4-[(6-hydroxy-2,5,7,8-tetramethyl-chroman-2-yl)methoxy]benzyl]-2,4-thiazolidinedione, and Compound 7: 5-[(7-benzyloxy-3-quinolyl)methyl]-2,4-thiazolidinedione.

The results set forth in Table 5 indicate that Compounds 6 and 7, which are the compounds of the formula (I) or the thiazolidine derivatives of the formula (III), improves body fat distribution.

Example 4: Decrease of cell Size of Mesenteric Adipose Tissue

A group consisting of five db/db female mice aged 16 weeks was prepared. To the group, the sample suspended in 1% aqueous solution of methyl cellulose was orally administered once a day for 16 days. Each of thus treated rats was dissected to collect the mesenteric adipose tissue, and then the tissue was sliced to prepare a paraffin specimen for microscope. After hematoxylin-eosin staining, two micrographs of each specimen were taken on color reversal films by means of an optical photomicrographic apparatus. From the micrographs, the area occupied by one adipocyte was measured by image analysis with a computer to obtain the average adipocyte area of the group. The results are set forth in Table 6.

TABLE 6

| Decrease of Cell Size of Mesenteric Adipose Tissue | | | |
|---|---|---|---|
| sample* | dose (mg/kg) | number of rats | cell area ($\mu m^2$) |
| Control | 0 | 5 | 3,921 |
| Compound 7 | 100 | 5 | 3,397 |

*) The sample is as follows: Compound 7: 5-[(7-benzyloxy-3-quinolyl) methyl]-2,4-thiazolidinedione.

The result set forth in Table 6 indicates that Compound 7, which is the compound of the formula (I) or the thiazolidine derivative of the formula (III), decreases cell size of the mesenteric adipose tissue.

Example 5: Pharmaceutical Example (tablets)

The tablets containing the following components were produced in an amount of 220 mg.

| components | | |
|---|---|---|
| active ingredient | 50 | mg |
| lactose | 103 | |
| starch | 50 | |
| magnesium stearate | 2 | |
| hydroxypropyl cellulose | 15 | |

Example 6: Pharmaceutical Example (Capsules)

The capsules containing the following components were produced in the amount of 350 mg.

| components | | |
|---|---|---|
| active ingredient | 40 | mg |
| lactose | 200 | |
| starch | 70 | |
| polyvinylpyrrolidone | 5 | |
| crystalline cellulose | 35 | |

[EFFECT OF THE INVENTION]

A compound of the formula (I) or a thiazolidine derivative of the formula (III) is advantageously employed as a visceral fat decreasing agent, a visceral fat accumulation inhibitor, and a body fat distribution improver.

What is claimed is:

1. A method for decreasing visceral fat comprising injecting or orally administering into a patient in need thereof a thiazolidine compound of the following formula (III) in an amount of 0.1 to 100 mg/day in the case of injection or in an amount of 1 mg/day to 10.0 g/day in the case of oral administration:

(III)

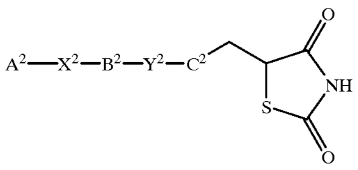

wherein $A^2$ represents an optionally substituted phenyl, pyridyl, oxazolyl or chromanyl group; $X^2$ represents a bond or $N(R^3)$ in which $R^3$ is a hydrogen atom, or an alkyl or aralkyl group; $B^2$ represents an optionally substituted alkylene chain; $Y^2$ represents a bond or an oxygen atom; and $C^2$ represents an optionally substituted benzene ring, quinoline ring, indole ring or benzothiophene ring.

2. The method of claim 1, wherein the thiazolidine compound has the following formula:

(IV)

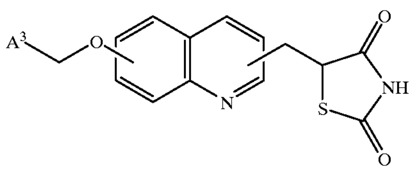

in which $A^3$ represents an optionally substituted phenyl or oxazolyl group.

3. The method of claim 1, wherein the thiazolidine compound is selected from the group consisting of 5-[(7-benzyloxy-3-quinolyl)methyl]-2,4-thiazolidinedione, 5-[4-[(6-hydroxy-2,5,7,8-tetramethylchroman-2-yl)methoxy]-benzyl]-2,4-thiazolidinedione, 5-[4-[2-(5-ethyl-2-pyridyl)ethoxy]benzyl]-2,4-thiazolidinedione, and 5-[4-[2-(methyl-2-pyridylamino)ethoxy]benzyl]-2,4-thiazolidinedione.

4. A method for inhibiting accumulation of visceral fat comprising injecting or orally administering into a patient in need thereof a thiazolidine compound of the following formula (III) in an amount of 0.1 to 100 mg/day in the case of injection or in an amount of 1 mg/day to 10.0 g/day in the case of oral administration:

(III)

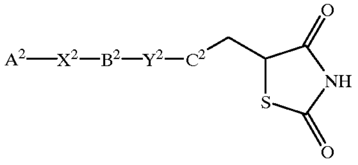

wherein $A^2$ represents an optionally substituted phenyl, pyridyl, oxazolyl or chromanyl group; $X^2$ represents a bond or $N(R^3)$ in which $R^3$ is a hydrogen atom, or an alkyl or aralkyl group; $B^2$ represents an optionally substituted alkylene chain; $Y^2$ represents a bond or an oxygen atom; and $C^2$ represents an optionally substituted benzene ring, quinoline ring, indole ring or benzothiophene ring.

5. The method of claim 4, wherein the thiazolidine compound has the following formula:)

(IV)

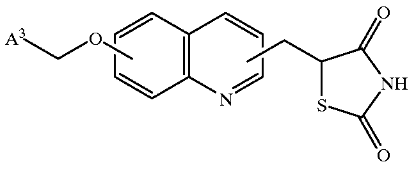

in which $A^3$ represents an optionally substituted phenyl or oxazolyl group.

6. The method of claim 4, wherein the thiazolidine compound is selected from the group consisting of 5-[(7-benzyloxy-3-quinolyl)methyl]-2,4-thiazolidinedione, 5-[4-[6-hydroxy-2,5,7,8-tetramethylchroman-2-yl)methoxy]-benzyl]-2,4-thiazolidinedione, 5-[4-[2-(5-ethyl-2-pyridyl)ethoxy]benzyl]-2,4-thiazolidinedione, and 5-[4-[2-(methyl-2-pyridylamino)ethoxy]benzyl]-2,4-thiazolidinedione.

7. A method for improving distribution of visceral fat comprising injecting or orally administering into a patient in need thereof a thiazolidine compound of the following formula (III) in an amount of 0.1 to 100 mg/day in the case of injection or in an amount of 1 mg/day to 10.0 g/day in the case of oral administration:

(III)

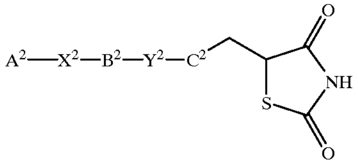

wherein $A^2$ represents an optionally substituted phenyl, pyridyl, oxazolyl or chromanyl group; $X^2$ represents a bond or $N(R^3)$ in which $R^3$ is a hydrogen atom, or an alkyl or aralkyl group; $B^2$ represents an optionally substituted alkylene chain; $Y^2$ represents a bond or an oxygen atom; and $C^2$ represents an optionally substituted benzene ring, quinoline ring, indole ring or benzothiophene ring.

8. The method of claim 7, wherein the thiazolidine compound has the following formula (IV):

(IV)

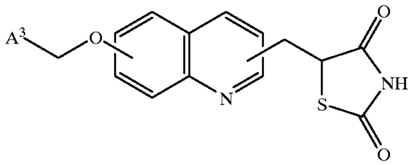

in which $A^3$ represents an optionally substituted phenyl or oxazolyl group.

9. The method of claim 7, wherein the thiazolidine compound is selected from the group consisting of 5-[(7-benzyloxy-3-quinolyl)methyl]-2,4-thiazolidinedione, 5-[4-[(6-hydroxy-2,5,7,8-tetramethylchroman-2-yl)methoxy]-benzyl]-2,4-thiazolidinedione, 5-[4-[2-(5-ethyl-2-pyridyl) ethoxy]benzyl]-2,4-thiazolidinedione, and 5-[4-[2-(methyl-2-pyridylamino)ethoxy]benzyl]-2,4-thiazolidinedione.

* * * * *